United States Patent [19]

Greenbaum

[11] Patent Number: 5,417,824

[45] Date of Patent: May 23, 1995

[54] CONVERSION OF ORGANIC SOLIDS TO HYDROCARBONS

[75] Inventor: Elias Greenbaum, Oak Ridge, Tenn.

[73] Assignee: Martin Marietta Energy Systems, Inc., Oak Ridge, Tenn.

[21] Appl. No.: 213,813

[22] Filed: Mar. 16, 1994

Related U.S. Application Data

[63] Continuation of Ser. No. 986,047, Dec. 10, 1992, abandoned.

[51] Int. Cl.$^6$ .................................................. C07C 4/00
[52] U.S. Cl. ........................... 204/157.15; 204/157.6; 204/158.2; 204/158.21
[58] Field of Search ............. 204/157.15, 157.6, 158.2, 204/158.21

[56] References Cited

U.S. PATENT DOCUMENTS

| | | | |
|---|---|---|---|
| 2,165,130 | 7/1939 | Coe | 260/406 |
| 2,553,944 | 5/1951 | Schlesman | 204/171 |
| 2,951,800 | 9/1960 | Sharp | 204/162 |
| 3,352,773 | 11/1967 | Schwartz et al. | 204/160.1 |
| 3,663,393 | 5/1972 | Latourette | 204/162 R |
| 4,608,137 | 8/1986 | Vaughan et al. | 204/129 |
| 4,609,444 | 9/1986 | Guillet | 204/157.6 |
| 4,917,784 | 4/1990 | Shelmutt | 204/157.6 |

OTHER PUBLICATIONS

Hon, "Formation of Free Radicals in Photo-irradiated Cellulose. IV. Effect of Ferric Ions." (1975) 2789-2797.
Hon, "Formation of Free Radicals in Photo-irradiated Celluose. III. Effect of Photosensitizers." (1975) 1933-1941.
Stillings, et al. "The Action of Ultraviolet Light upon Cellulose. I. Irradiation Effects. II. Post Irradiation Effects." (1942) 753-760.
Desai, et al. "The Photochemical Degradation of Cellulose Material." (1968) 134-144.
Kleinert, "Free Radical Reactions in UV Irradiation of Cellulose." 1964) 24-28.
Savastenko, et al. "Investigation of the Discharge of Gaseous Products During the Photolysis of Cellulose Mixed With Carboxymethylcellulose." (1979) 1-5.

Primary Examiner—John Niebling
Assistant Examiner—C. Delacroix-Muirheid
Attorney, Agent, or Firm—Harold W. Adams; Joseph A. Marasco; Edward A. Pennington

[57] ABSTRACT

A method of converting organic solids to liquid and gaseous hydrocarbons includes impregnating an organic solid with photosensitizing ions and exposing the impregnated solid to light in a non-oxidizing atmosphere for a time sufficient to photocatalytically reduce the solid to at least one of a liquid and a gaseous hydrocarbon.

16 Claims, 4 Drawing Sheets

CONVERSION OF ORGANIC SOLIDS TO HYDROCARBONS

This invention was made with Government support under contract DE-AC05-84OR21400 awarded by the U.S. Department of Energy to Martin Marietta Energy Systems, Inc. and the Government has certain rights in this invention.

This is a continuation of application Ser. No. 07/986,047, filed on Dec. 10, 1992, abandoned.

FIELD OF THE INVENTION

The present invention relates generally to the conversion of carbon-based solids, such as biomass, to gaseous and liquid hydrocarbons, and more specifically, to the preparation of biomolecular materials that are transformed to such hydrocarbons photocatalytically. Photosensitizing ions, such as ferric ions in the form of ferric chloride, are impressed into the biomass. The impregnated biomass then becomes photocatalytically active and is subsequently transformed into liquid and gaseous hydrocarbons.

BACKGROUND OF THE INVENTION

The supply of fossil hydrocarbons is finite, and eventually will be depleted. Nonetheless, the world economy depends heavily on such hydrocarbons for the production of fuels and petrochemical feedstocks, for example.

It has become apparent that the combustion of fossil fuels may cause irreversible harm to the environment. An example is the increased level of atmospheric carbon dioxide directly traced to the burning of fossil fuels. Studies have shown that increased levels of atmospheric carbon dioxide can have adverse effects on the earth's climate through such mechanisms as "global warming", accompanied by major alterations of weather patterns. Needless to say, an alternative, preferably renewable energy source which would obviate fossil fuels has long been sought.

It is well known that the process of green plant photosynthesis converts light energy into stored chemical energy. In this process, atmospheric carbon dioxide is converted to reduced organic matter such as cellulose, hemicellulose, and lignins. However, biomass is not an ideal form for fuel or chemical feedstock use since it is a solid containing varying levels of water and oxygen. These latter components reduce the fuel value of the biomass.

Various approaches have been undertaken to transform biomass into a fuel or chemical form that is more valuable. For example, gasification and pyrolysis of wood have been described in *Organic Chemicals From Biomass*, edited by I. S. Goldstein, CRC Press, Boca Raton (1981) (p. 5 for gasification and pp. 63-99 for pyrolysis). In these approaches, biomass is heated in the absence or restricted presence of oxidizing agents such as oxygen, water, and carbon dioxide. In the presence of wood, pyrolysis processes are alternatively referred to as carbonization, wood distillation, or destructive distillation processes. As generally accepted, carbonization refers to processes in which the char is the principal product of interest. Wood distillation refers to liquids produced, whereas destructive distillation refers to both char and liquids. The reaction conditions for gasification and pyrolysis require high temperatures and pressures. Also, under these extreme process conditions, little opportunity is available to control the composition of products. These techniques are basically the same as those used in the processing of coal and yield analogous products.

Instead of subjecting the biomass to reaction conditions which cause simultaneous conversion of all its components, an alternative approach is to choose reactions which selectively convert one component at a time. For example, it is known that cellulose can be converted to glucose by acid hydrolysis. However, acid hydrolysis, in its dilute or concentrated versions is limited in a number of ways. The glucose produced is in aqueous solution, and in dilute acid hydrolysis yields are limited. In concentrated acid hydrolysis, high capital and operating costs are associated with corrosion-resistant equipment and acid recovery and loss.

An alternative method of converting the cellulose fraction of biomass to a fuel is the enzymatic hydrolysis of cellulose. In this method of conversion, an aqueous cellulose suspension is incubated with cellulase enzymes. The enzymatic activation of cellulase causes the hydrolysis of cellulose. The hydrolysis product is glucose. Although this process results in the production of glucose from cellulose, additional process steps such as fermentation and/or water removal are required. Although enzymatic hydrolysis of cellulose can provide 100% yield of glucose, the reaction is much slower than acid hydrolysis, requiring days rather than hours or minutes for completion. Moreover, enzymatic hydrolysis is inhibited by the presence of lignin, which is a major component of most biomass.

U.S. Pat. No. 4,608,137 to Vaughen describes the gasification of carbonaceous material in hydrogen manufacture using divalent iron oxidation as anode reaction and recycled anolyte regenerated by reducing ferric ions with carbon. In this work, hydrogen was manufactured from recycled aqueous electrolyte having pH 3 or less and containing $Fe^{2+}$ ions. $Fe^{2+}$ is oxidized to $Fe^{3+}$ at anode and hydrogen is generated at cathode. U.S. Pat. No. 3,352,773 to Schwartz et al. describes a method of degrading polysaccharides using light radiation and a water-soluble metal or nitrogen based salt of nitrous or hyponitric acid. Cellulosic materials are converted to saccharides of lower molecular weight by irradiation with light.

SUMMARY OF THE INVENTION

An object of the present invention is to provide a new composition of matter and method employing same for the production of hydrocarbons.

Another object of the present invention is to provide a renewable source of hydrocarbons using a method that employs readily available sources of biomass impregnated with photosensitizers.

Another object of the present invention is to provide a method of producing hydrocarbons from biomass in which catalysts are used to control the chemical composition of the products of photoreaction when a biomass is transformed to hydrocarbon.

Still another object of the present invention is to provide a simple and economically feasible method for the direct conversion of wood, paper, and almost any solid biomass into short chain hydrocarbons.

These and other objects of the invention are met by providing a method of converting organic solids to liquid and gaseous hydrocarbons which includes the steps of impregnating an organic solid, such as wood or other fibrous material, with photosensitizing ions such as ferric ions in the form of ferric chloride, and exposing the impregnated solid to light, preferably UV light, in a non-oxidizing atmosphere to photocatalytically reduce the solid to liquid and gaseous hydrocarbons.

Other objects, advantages and salient features of the invention will become apparent from the following detailed description, which taken in conjunction with the annexed drawings, discloses preferred embodiments of the invention.

DETAILED DESCRIPTION OF THE INVENTION

The new method and composition of matter of the present invention involves the production of organic fuels and chemical feedstocks from cellulose- and lignin-containing materials such as biomass. The following examples, taken in conjunction with the Figures, provide a detailed description of the preferred embodiments of the present invention.

Example I

According to the methodology of the present invention, organic solids are converted to liquid and gaseous hydrocarbons by impregnating an organic solid, such as wood or other fibrous material, with photosensitizing ions such as ferric ions in the form of ferric chloride, and exposing the impregnated solid to light, preferably UV light, in a non-oxidizing atmosphere to photocatalytically reduce the solid to liquid and gaseous hydrocarbons.

Figure 1:
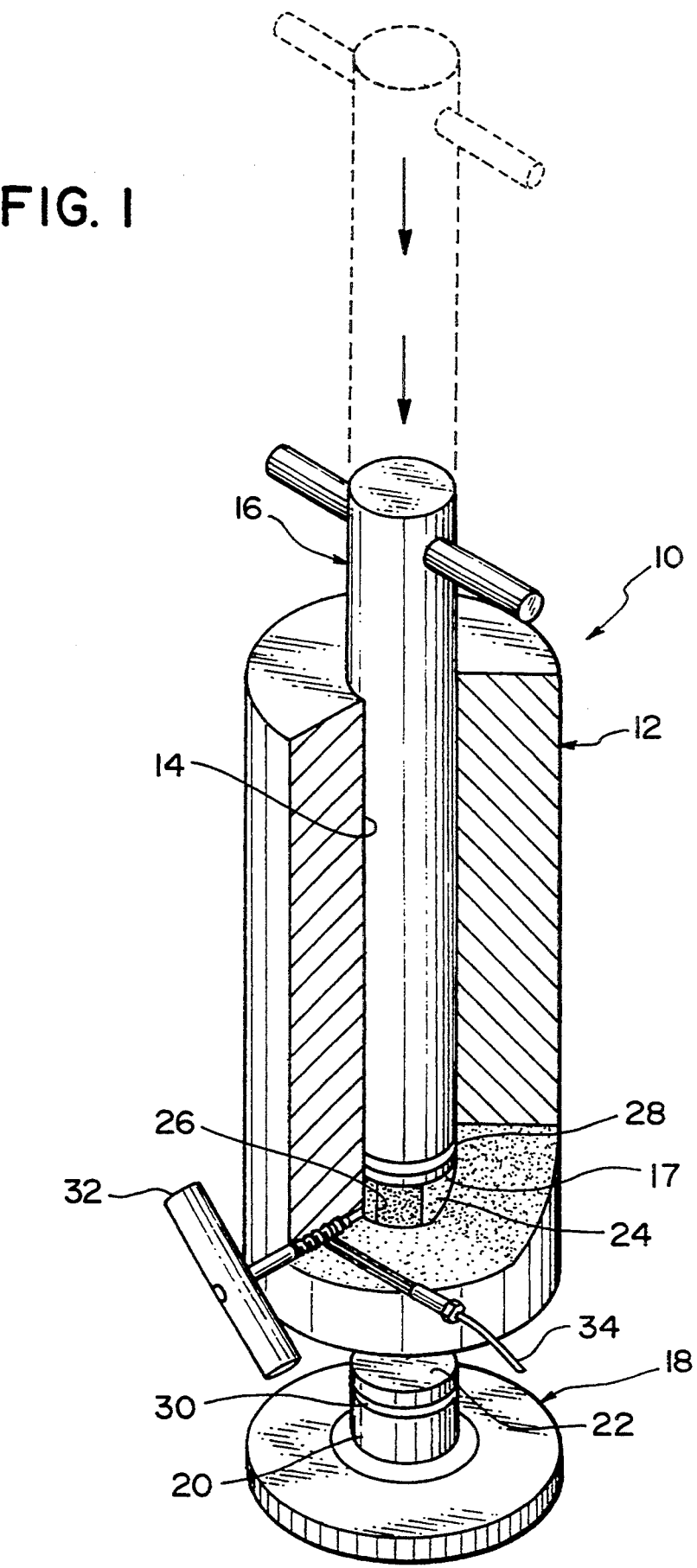
FIG. 1 is a perspective view, partially cut-away, of a high-pressure apparatus for impregnating a sample of biomass according to the present invention.

FIG. 1 is a perspective view, partially cut-away, of a high-pressure apparatus 10 for impregnating a sample of biomass. A body 12 has a cylindrical bore 14 which slidably receives a piston 16 having an inner end 17. A bottom plate 18 has a piston 20 mounted thereon so that the piston is received in the cylindrical bore 14 when the bottom plate 18 is fixedly mounted on the lower end of the body 12.

The inner end 22 of the piston 20 and the inner end 17 of the piston 16 define a pressure chamber 24, the volume of which varies with the position of the piston 16. A piece of wood 26 is placed in the pressure chamber 24, which is then filled with a photosensitive solution so as to completely immerse the wood 26. The piston 16 has an O-ring seal 28 on its inner end portion, and the piston 20 has an O-ring 30.

A downward force is applied to the piston 16, as indicated by the directional arrows, to increase the pressure in the chamber 24. Because of the relative incompressibility of the liquid, pressure is built up in the pressure chamber 24. The result of the high pressure is to force the photosensitizing solution into the fibers of the biomass or wood 26. An example of a preferred photosensitizing solution is ferric chloride, which is commercially available. In a typical batch process, the pressure would be 20,000 psi, which would be held for about five minutes.

Figure 2:
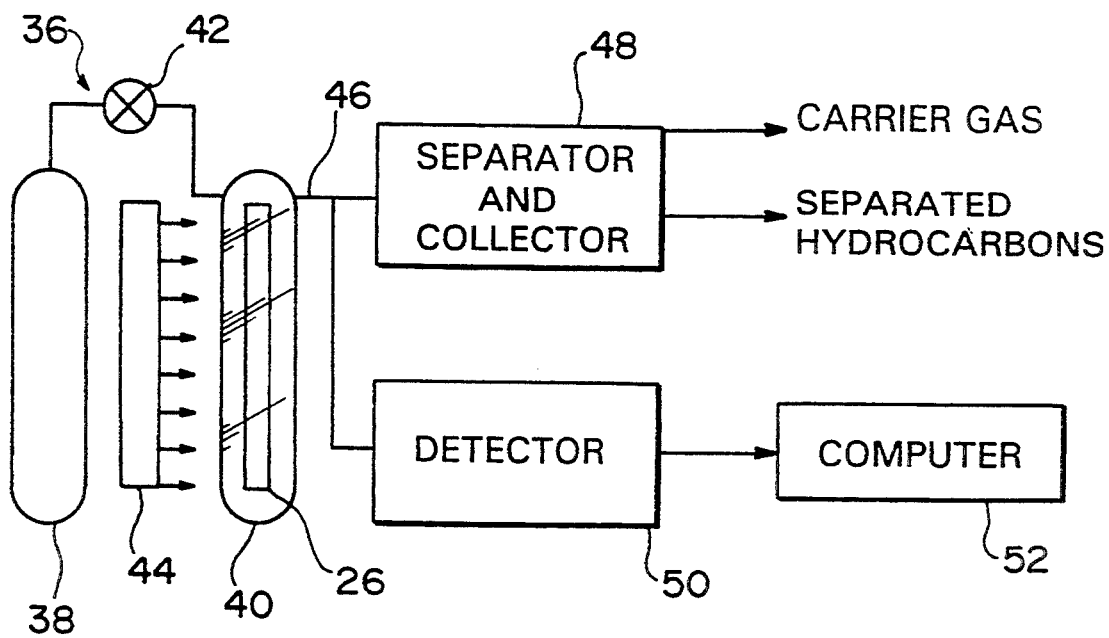
FIG. 2 is schematic view of an apparatus used to produce hydrocarbons from impregnated biomass according to the present invention.

After the force is released, a drain valve 32 is opened and the solution is drained through a drain 34. The wood 26 is then extracted from the chamber 24 and has thus been transformed into a photochemically active sample, ready to be placed in a flow system such as the one schematically illustrated in FIG. 2. As seen in FIG. 2, a flow system 36 includes a source 38 of compressed gas (e.g., helium) which serves as a carrier gas. A photoreaction cell 40, containing the impregnated sample of wood 26, is in fluid communication with the source 38 of carrier gas. A control valve 42 is disposed in the line connecting the carrier gas inlet of the photoreaction cell 40 to the outlet of the source 38. The photoreaction cell 40 is transparent to ultraviolet (UV) light, and is preferably made of transparent quartz.

A UV light source 44 is positioned next to the photoreaction cell 40 so as to irradiate the impregnated wood 26 to its radiating light beams (indicated as arrows). Any commercially available UV light source can be used, preferably a xenon or mercury lamp producing wavelengths in the absorption range of the photosensitizing solution. For ferric chloride, this is in the range of 300–450 nm. The helium in the photoreaction chamber 40 creates a non-oxidizing atmosphere, and the photosensitizing solution photocatalytically reduces the solid wood 26 to gaseous hydrocarbons when the biomass is exposed to UV light. Of course, the photoreaction chamber must be made of material transparent to UV light, such as quartz.

The gaseous hydrocarbons are removed, along with the carrier gas, through an outlet 46. The outlet delivers a mixture of carrier gas and gaseous hydrocarbons, such as methane, to a separator and collector 48. The separator and collector 48 separates the carrier gas from the gaseous hydrocarbons. Any commercially available separator can be used, such as a liquid nitrogen trap which traps the photoproduced gases. The separated carrier gas can either be vented to atmosphere, recycled, or otherwise disposed of, while the hydrocarbons are collected and stored using any suitable means.

The outlet 46 is also coupled to a detector 50, which takes a sample of the extracted mixture of carrier gas and hydrocarbon gas and determines the quantity of hydrocarbon gas. Any commercially available detector can be used, such as a Model 23–700 Total Hydrocarbon Gas Analyzer manufactured by Gow-mac Instrument Company of Bound Brook, N.J. (USA). An electrical signal indicative of the quantity of hydrocarbon gas is output to a computer 52 which can display data indicative of the hydrocarbon production rate.

Data generated by the detector 50 can be used to determine when a batch of biomass or wood 26 has been transformed to hydrocarbon, so that subsequent batches can be processed. Moreover, data reflecting the rate of production can be used to analyze the effectiveness of the chosen photosensitizer solution.

Not shown in FIG. 2 for simplicity various components of the flow system which would be obvious to use by persons skilled in the art of gas measurement and analysis. These include, as needed, bubbler cell for humidification, gas blenders for absolute calibration of the hydrocarbon detector 50, a Hersch electrogalvanic cell for oxygen measurement, electrolysis cell for calibration of the Hersch cell, desiccants for drying the gas, etc.

Figure 3:
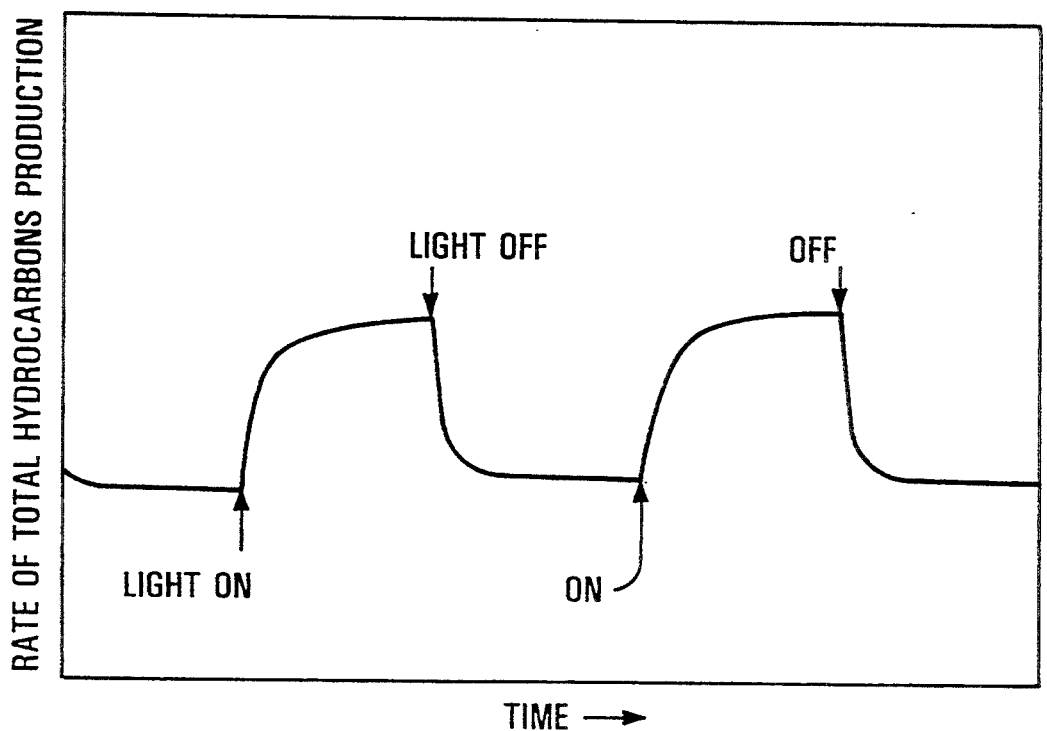
FIG. 3 is a graph of data taken during processing of a biomass sample according to the present invention.

FIG. 3 is a graph of data taken during processing of a biomass sample according to Example I. Prior to "LIGHT ON", a base line was established. At LIGHT ON, hydrocarbon production was measured. At "LIGHT OFF", hydrocarbon production returns to baseline.

It is important to note that volatile hydrocarbons production occurred in a helium atmosphere. This proves that the carrier gas does not participate in the photochemistry of hydrocarbons production. It therefore follows that the wood (or other biomass) serves as both source of chemical reductant and carbon for the synthesis of volatile hydrocarbons. However, if a different carrier gas, such as nitrogen, were used it can participate in the photochemistry. With appropriate catalysts, nitrogen reduction compounds, such as ammonia, can be photoproduced.

Example II

Wood is a mixture of cellulose, hemicellulose, and lignin. Lignin is a hydrocarbon material. Pure microcrystalline cellulose is placed in the photoreaction cell 26 following impregnation with ferric chloride as the photosensitizer solution, and volatile hydrocarbons were produced. The carrier gas was helium, as in the case of Example I. Thus, cellulose can undergo a disproportionation reaction in which it serves as source of reductant and carbon for hydrocarbons synthesis.

During impregnation, the white crystalline cellulose took on the mustard-yellow color of the ferric chloride solution. The ferric chloride-impregnated cellulose was entrapped on a filter pad and placed in the photoreaction chamber 40 of the flow apparatus of FIG. 2.

Figure 4:
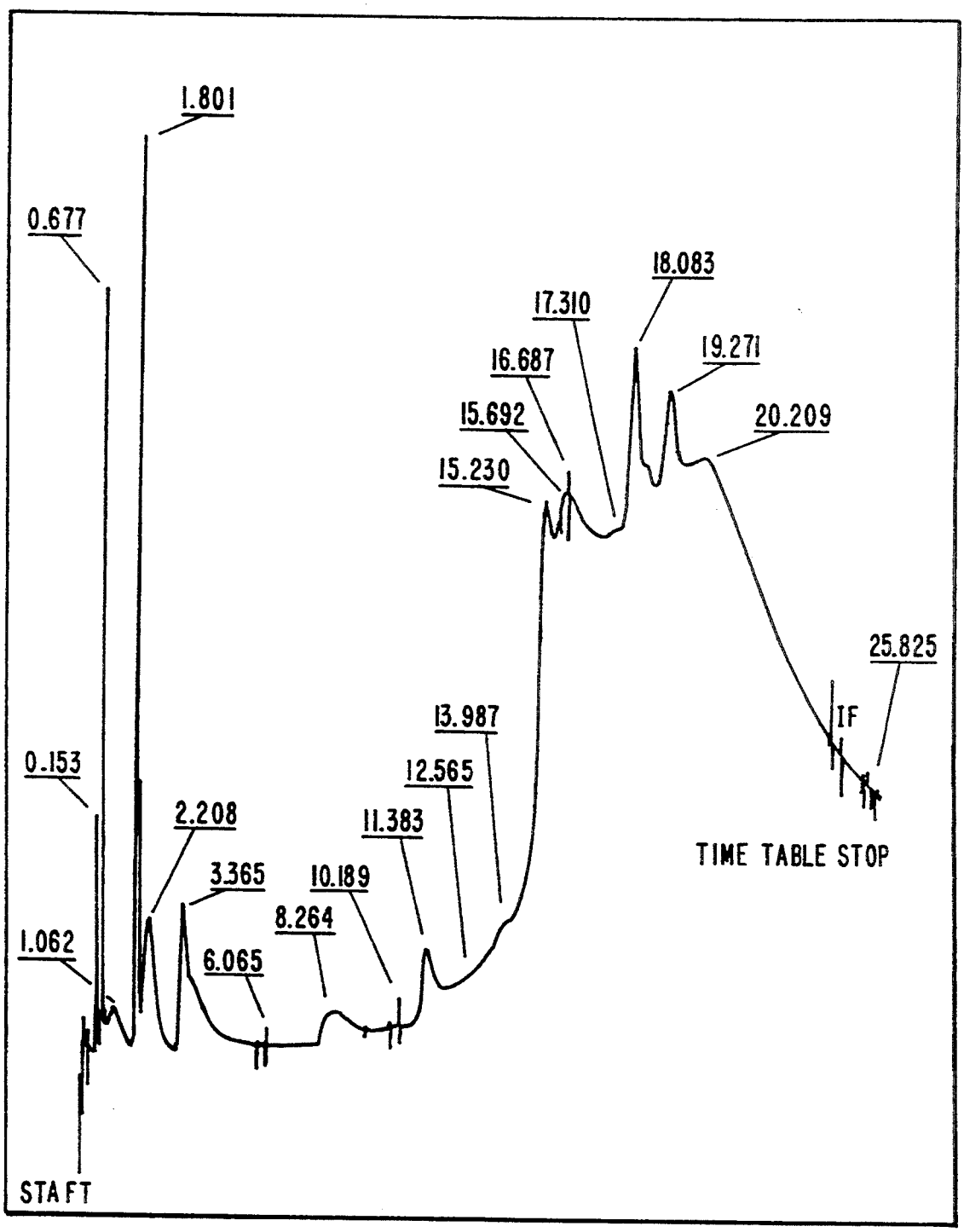
FIG. 4 is a gas chromatogram of a sample of the photoproduced hydrocarbons of the present invention.

FIG. 4 is a graph reading of a gas chromatogram of a sample of the photoproduced hydrocarbons. The analyzer or detector 50 of FIG. 2 can only detect total hydrocarbons, without distinguishing the type of hydrocarbons produced. A gas chromatograph can be used to provide information on the distribution of hydrocarbons that are produced. The chromatogram of FIG. 4 was produced as follows. A liquid nitrogen trap was placed in line in the flow system downstream from the photoreaction chamber 40. The hydrocarbons were trapped in the liquid nitrogen trap, while the helium carrier gas flowed on through. After a period of hydrocarbon production and trapping, bellows shut-off valves at the inlet and outlet of the liquid nitrogen trap were shut, the trap was removed from the flow system and from the liquid nitrogen bath.

The trap containing the hydrocarbon sample was fitted with a rubber septum port through which a gas tight sampling syringe could withdraw a sample of the volatile hydrocarbons and be injected into the sample port of a gas chromatograph. The peak at 0.677 min. was positively identified as methane with the use of a methane in helium standard. The remaining peaks, although not specifically identified here, represent a distribution of other higher molecular weight hydrocarbons.

A visual inspection of the post-irradiated material revealed a black charcoal-like material remaining on the entrapped filter pad. This was probably carbon. One possible photochemical reaction occurring in the reaction cell is $$(CH_2O)_2 + light \rightarrow CH_4 + C + O_2$$

The equation above predicts that molecular oxygen should be simultaneously photoproduced with the methane. A Hersch electroanalytical oxygen sensor was place in line in the helium carrier downstream from the reaction cell. The simultaneous photoevolution of methane and oxygen was observed, as suggested by the equation.

Figure 5:
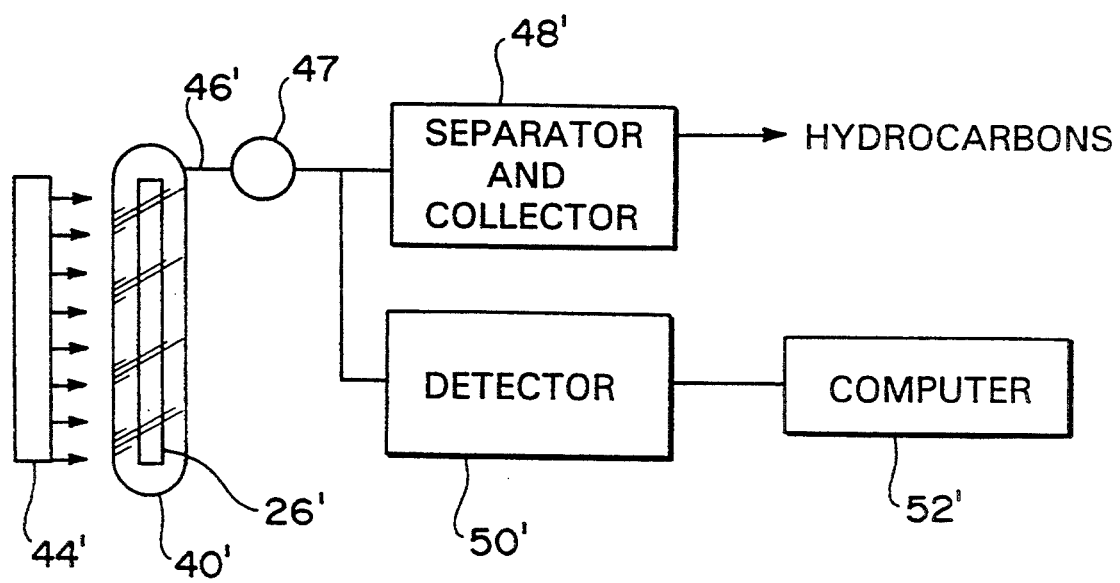
FIG. 5 is schematic view of an apparatus used to produce hydrocarbons from impregnated biomass according to another embodiment of the present invention.

In either example described above, the hydrocarbons can be removed from the photoreaction chamber by vacuum, instead of using the carrier gas source. FIG. 5 illustrates such an embodiment, in which components common to the embodiment of FIG. 2 have the same, but primed, reference numerals. In the FIG. 5 embodiment, a vacuum pump 47 is used instead of a positive-pressure carrier gas in order to cause hydrocarbon gas to flow out of the reaction chamber 40'. The separator and collector 48' collects the hydrocarbon gas which can be delivered through appropriate means to storage containers (not shown).

In both the examples described above the reactions occurred at room temperature and at normal atmospheric pressures. Thus, the process of the present invention has the advantage of being energy efficient and results in the direct photoconversion from solid biomass, such as wood, to hydrocarbons. The characteristic photoproduced hydrocarbons can thus be determined by the selection of light sources (intensity and wavelength), photosensistizers, catalysts, and atmosphere. The particular choices of these and other parameters will optimize pathways for a specifically desired end product.

Any photosensitizing ions can be used, preferably in solution so as to facilitate impregnation of the biomass. In addition to ferric ions, iron-, cobalt-, nickel-, manganese-, and chromium-based photosensitizers can be used. Also, the photosensitizers can be sulfates and nitrates, in addition to chlorides. However, these are mentioned as examples. Virtually any inorganic ions capable of undergoing an oxidation-reduction reaction can be used. Some semiconductors can also be used, such as titanium dioxide, zinc oxide and tungsten oxide.

The invention provides a simple and economically feasible method for the direct conversion of wood, paper, and almost any solid biomass into short chain hydrocarbons ($CH_4$—$C_5H_{12}$). The examples described above produced gaseous hydrocarbons. It is expected that, depending on the biomass, photosensitizing ions, and other parameters selected, a liquid hydrocarbon could also be produced.

While advantageous embodiments have been chosen to illustrate the invention, it will be understood by those skilled in the art that various changes and modifications can be made therein without departing from the scope of the invention as defined in the appended claims.

What is claimed is:

1. A method of converting lignocellulosic materials to liquid and gaseous hydrocarbons comprising the steps of:

impregnating the lignocellulosic materials with a solution containing photosensitizing ions; and exposing the impregnated materials to light in a nonoxidizing atmosphere for a time sufficient to photocatalytically reduce the solid to at least one of a liquid and a gaseous volatile hydrocarbon which is more reduced than a cellulosic constituent of the lignocellulosic materials.

2. A method according to claim 1, wherein the lignocellulosic material is a biomass material.

3. A method according to claim 2, wherein the biomass is selected from the group consisting of wood, paper, lignin, agriculture residues, and algae.

4. A method according to claim 1, wherein the photosensitizing ions are ferric ions.

5. A method according to claim 4, wherein the ferric ions are selected from the group consisting of ferric chloride, ferric nitrate and ferric sulphate.

6. A method according to claim 1, wherein the light is UV light.

7. A method according to claim 1, wherein the lignocellulosic material is wood, the photosensitizing ions are ferric ions, and the light is UV light.

8. A method according to claim 1, wherein the photosensitizing ions are inorganic ions in solution and being capable of undergoing an oxidation-reduction reaction when exposed to UV light.

9. A method according to claim 1, wherein the exposing step comprises placing the impregnated materials in a reaction chamber, and maintaining the reaction chamber substantially at room temperature and at normal atmospheric pressure.

10. A method according to claim 9, further comprising flowing a carrier gas through the reaction chamber to remove gaseous hydrocarbons produced therein.

11. A method according to claim 10, wherein the carrier gas is helium.

12. A method according to claim 9, further comprising creating a vacuum downstream of the reaction chamber to remove gaseous hydrocarbons produced therein.

13. The method according to claim 1, wherein said lignocellulosic material is a fibrous organic material.

14. A process according to claim 1, wherein said photosensitizing ions are obtained from $TiO_2$, $ZnO$, zinc, or $WO_3$.

15. The process according to claim 1, wherein the impregnating up step includes immersing the lignocellulosic material to be impregnated in a solution containing photosensitive ion in a closed chamber and applying pressure to the solution to forcibly impregnate the material with the solution.

16. A method of converting lignocellulosic materials to liquid and gaseous hydrocarbons comprising the steps of:

impregnating the lignocellulosic materials with a solution containing photosensitizing ions; and exposing the impregnated materials to light in a non-oxidizing atmosphere for a time sufficient to photocatalytically reduce the solid to at least one of a liquid and a gaseous volatile hydrocarbon and oxygen, wherein the volatile hydrocarbon is more reduced than a cellulosic constituent of the lignocellulosic materials.

* * * * *